United States Patent [19]
Trnka et al.

[11] Patent Number: 5,858,357
[45] Date of Patent: Jan. 12, 1999

[54] PHARMACEUTICAL COMPOSITION CONTAINING AN ISOLATED PROTEASE PROENZYME, AMYLASE, AND APROTININ

[76] Inventors: Frantisek Trnka, No. 42 Cechova, 370 01 Ceské Budéjovice, Czech Rep.; Miroslav Rybak, 573 Nesporova, 149 00 Praha 11, Czech Rep.; Roman Marek, No. 40 Nad Piskovnou, 140 00 Praha 4, Czech Rep.; Ladislav Vavra, No. 2 Klavikova, 370 04 Ceské Budéjovice, Czech Rep.

[21] Appl. No.: 649,184

[22] Filed: May 17, 1996

[30] Foreign Application Priority Data

May 17, 1995 [CZ] Czech Rep. .............................. 1272-95

[51] Int. Cl.$^6$ .......................... A61K 38/48; A61K 38/54; C12N 9/26; C12N 9/76
[52] U.S. Cl. .................. 424/94.64; 424/94.2; 424/94.21; 424/94.3; 424/94.6; 424/94.63; 435/184; 435/201; 435/202; 435/204; 435/213; 435/218; 435/220; 435/226
[58] Field of Search ................ 424/94.21, 94.2, 424/94.3, 94.6, 94.63, 94.64; 435/184, 201, 213, 218, 202, 204, 220, 226

[56] References Cited

U.S. PATENT DOCUMENTS 3,956,483 5/1976 Lewis ................................... 424/94.21

OTHER PUBLICATIONS

Rawn, Biochemistry, Harper & Row, Publishers, Inc., NY, NY, pp. 214–218 and 479, 1983.

Sigma Catalog, pp. 125 and 586, 1991.

*Primary Examiner*—David M. Naff
*Assistant Examiner*—Janet M. Kerr
*Attorney, Agent, or Firm*—Todd E. Garabedian; Wiggin & Dana

[57] ABSTRACT

The invention is directed to a pharmaceutical preparation with a modulatory effect on malignant tumors, which contains a combination of protease proenzymes and amylases in a ratio between 1:100 and 100:1 in enzymatic activity units, and a protease inhibitor. The invention is also directed to use of such a preparation to modulate the effects of malignant tumors in humans and animals.

3 Claims, 1 Drawing Sheet

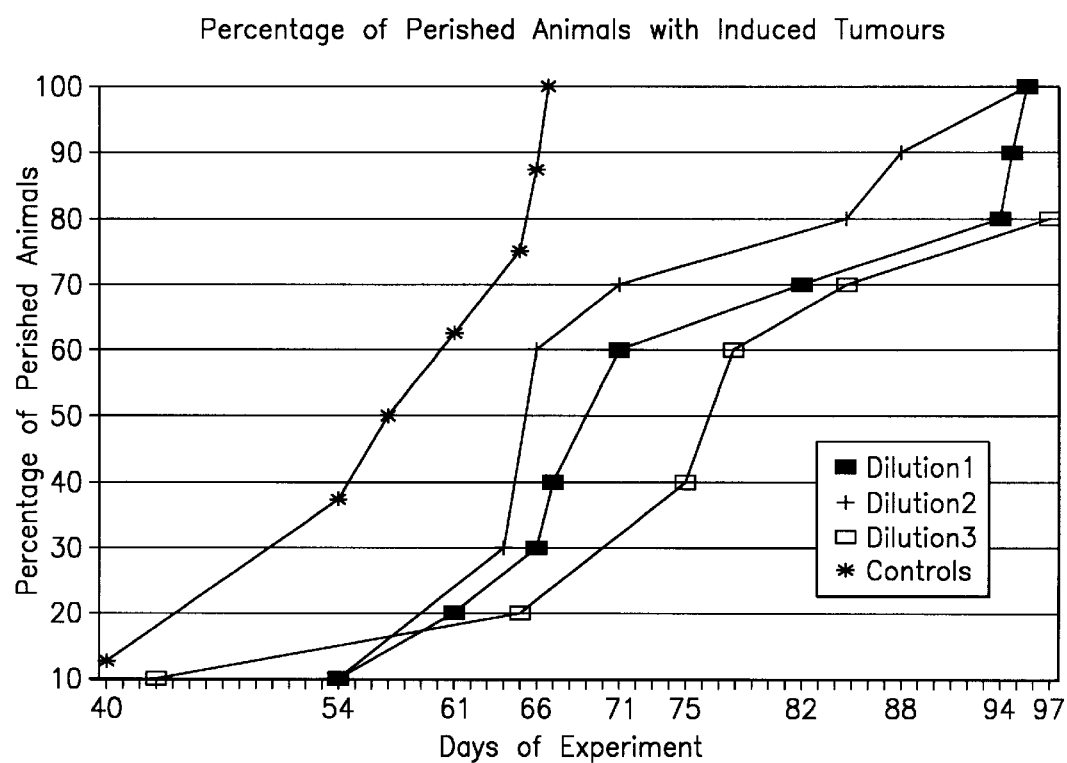

PHARMACEUTICAL COMPOSITION CONTAINING AN ISOLATED PROTEASE PROENZYME, AMYLASE, AND APROTININ

FIELD OF THE INVENTION

The invention concerns enzymatic organopreparations consisting of protease proenzymes and amylase, suitable for pharmacological influencing of biological responses of the organism during its interaction with malign tumours. These preparations are utilisable in human and veterinary medicine.

BACKGROUND OF THE INVENTION

Current oncological therapy utilises mostly eradicative methods such as surgery and actinotherapy, striving to eradicate or at least reduce the primary tumour. An accompanying assumption is that the remaining latent tumour population will be eradicated by natural immunological surveillance of the organism itself. This basic therapeutic approach is modified by adjutant and lately also nonadjuvant chemotherapy. The utilised therapeutic combination represents thus a compromise between the positive therapeutical and negative immunosuppressive effect of all the a.m. methods and individual cancerogenic effect of actinotherapy and chemotherapy. For complexities sake should be mentioned also therapy with hormones, which methodically represents a class of chemotherapy including the a.m. negative, i.e., immunosuppressive and cancerogenic effects. The resulting positive effect of such combined therapy is thus based on a significant immune tolerance of the organism both towards the existing disease and therapy as such. Such a situation is neither the rule nor happens often. Subsequent or simultaneous therapeutical efforts leading to immunomodulation through immunotherapy thus are logically doomed to failure due to the extent of disease and the extend of tissue catabolism. As part of the contest for valid oncological therapy, there is currently a renaissance of enzymotherapy, a method essentially rooted in the first case of this century (Beard, Chadto et Windus, London 1911). Their successors were Freund and Kaminer (Freund E., Kaminer G., Springerverlag, Wien 1925, Freund E., Med.Wschr., 12, 1934) and Christiani (Christiani A., Krebsforsch., 1938, 47, 176). Theoretical and experimental findings of these authors were then followed by clinical studies of Wolf and Benitez, Wolf and Ransberger (Wolf M., Ransberger K., Enzymtherapie, Maudrich. Wien 1970). These authors showed the selective oncolytic effect of animal and plant hydrolases (proteases) and participation of various enzymes in potentiation of the oncolytic effect. These authors also observed enteral resorption of hydrolases and glycosidases (amylases) and laid the foundations for peroral therapy including the WOBE MUGOS (trademark of Mucos Pharma GmbH, Geretsried, Germany) combinations of enzymes (e.g., papain, trypsin and calf thymus) for therapeutical use.

Systemic enzymotherapy is based on clinical utilisation of experimental data about effects of active proteases. These are systemic antiinflammatory effects and effects on fibrinolysis, stimulation of cytokine production (TNF-alpha, IL 2,6), stimulation of polymorphonuclear leukocyte production and of the macrophage system. Concerning local antitumour effects there appears among others a selective oncolytic effect leading to diminishing the efficacy of tumour cell membrane adhesive molecules and together with systemic fibrinolytic activity also prevention of metastase formation. There should be also mentioned the paper of Yoneda et al. (Yoneda et al., Cancer Res., 1994 54, 2509), who, after application of a partially purified extract of pork pancretic cells to mice with a human spinocellular skin tumour observed a beneficial effect on anorexia, weight loss, development of cachexia and survival times. The authors partially purified the pancreatic factor without defining its effective substance.

When using active proteases for therapy one has to take into account some facts, which limit the effect of such therapy. These are:

a) Pancreatic proteases in the blood stream and interstitium are rapidly inactivated by present polyvalent inhibitors (alpha-1 protease inhibitor, antithrombin III, C1-inhibitor and chymotrypsin inhibitor). Possible disruption of the alpha 2-macroglobulin protease complex in the presence of a substrate with high affinity for the protease was proven for many proteolytical systems (e.g., alpha 2—macroglobulin (MG)—plasmin-fibrin), but for the system alpha 2—macroglobulin (MG)—trypsin-trypsin receptor remains still only a theoretical consideration. An advantage of the inhibitor-protease bond is a decrease in antigenicity of the foreign protease due to complex formation.

b) Trypsin-like proteases in a similar way to other proteases (i.e. lysosomal cathepsin B) can increase the degree of invasivity of tumour cells through destruction of surrounding host tissue (Koivanen E., Int. J. Cancer 1991, 47 (4), 592)).

c) Trypsin can influence the blood protease system, which is internally related by activation and inhibition mechanisms (trypsin influences detrimentally the coagulation—fibrinolytic system, and directly leads to formation of kinins, mediators of inflammation and pain, from plasmatic kininogens, etc.)

SUMMARY OF THE INVENTION

The subject of the application is a pharmaceutical preparation having a modulatory effect on malign tumours. Its essence is based on its contents of a) protease proenzymes b) amylase in a ratio between 1:100 and 100:1 in enzymatic activity units.

Protease proenzymes that may be included are one or more of a group containing trypsinogen chymotrypsinogen proelastase and prekallikrein The preparation can contain amylase of human, animal, bacterial or plant origin and the protease proenzymes can be either of human or animal origin.

The pharmaceutical preparation can contain as an extra component a polyvalent protease inhibitor, such as aprotinin.

Finally the invention covers utilization of a combination of protease proenzymes and amylases for production of drugs with a modulatory effect on malign tumours.

DESCRIPTION OF THE DRAWINGS

The invention will be more fully understood from the following detailed description taken in conjunction with the accompanying drawing in which:

The FIGURE is a graph of the percentage of perished animals as a function of time.

DETAILED DESCRIPTION OF THE INVENTION

Theoretical foundation for tumour cell modulation is represented by a purely biological approach to cancerogenesis and efforts towards tumour modulation. The malign tumour is thus considered to represent an "ectopic pregnancy" resulting out of primordial gonocytes getting stuck during migration into the gonades. This "ectopic pregnancy" loses those regulatory mechanisms regulating normal pregnancy. Among these is especially important regulatory effect of the embryo on the triphoblast, which is considered to represent an analogy to malign tumours. As a unique physiological quality existing in nature the trophoblast invades, metastases and grows infinitely in situations where the embryo is lacking (molar syndromes, complicated molla or choriocarcinoma). It has been observed that during final phases of organogenesis, in the so called critical period the embryo influences and stops trophoblast proliferation. The trophoblast differentiates, syntitiotrophoblast tissues appear and the up to that moment rapid mitosis ceases. If the embryo is lacking or it is malformed, this "braking" effect and trophoblast differentation do not materialize. This leads to creation of a choriocarcinoma, which is considered to be the fundamental model of malignancy origin. In trying to influence and simulate embryological regulation embryonal extracts were used—the most effective of these were pancreatic extracts of newborn lambs, calves and piglets. Later a mix of two enzymes—trypsin and amylase—were used. Certain effects in influencing the trophoblast were observed but this method was not reproducible at all (Beard, Chadto et Windus, London 1911).

According to the invention, utilisation of protease proenzymes, especially trypsinogen and amylase has in contrast to current enzymotherapy the following characteristics:

1. Application of active proteases for the a.m. use is considered to represent a nonphysiological challenge of the organism.

2. Application of protease proenzymes as sources of active protease in situ (in the tumour) is more physiological then application of active proteases.

3. The organism is less vulnerable to the danger of detrimental processes such as influencing the kallikrein-kininkininase system, activation of coagulation and fibrinolytic system leading to disseminated intravascular coagulation, possibility of active protease attack on the tissues (i.e. of the colon). These dangers are almost nonexistent when using proenzymes.

4. Interaction with inhibitors, coupled often with irreversible protease inactivation and creation of circulating enzyme-inhibitor complexes is only minimal when using protease proenzymes.

Based on multiple criteria a model of the activity mechanism was created based on the assumption that activation of proenzymes to effective enzyme molecules takes place on the surface of the tumour cell through action of activators present only in malignant cells and absent in the healthy cell. Presence of such activators was documented by many tumour cells. The a.m. assumption about effector mechanism is supported by the observation that protease inhibitors are present on benign tumour cells but not on malignant ones (Bohe J., Bohe M., Lindstroem M., Ohlsson K., J. Clin. Pathol. (1990), 43, 901). Highly nonspecific proteases such as trypsin have a high probability of cutting peptide chains of the cell wall in vicinity of basic amino acids arginine, lysine and histidine. Amylase, which is a necessary component of the claimed invention complements the effect of proteases by splitting of the carbohydrate element of surface glycoproteins of the malign cell. Proteases facilitate such an effect.

Activation and protease effect take place on the surface of the tumour cell and its immediate vicinity. Because of their intact character the protease proenzymes will not contribute to increasing the invasivity of tumour cells as active proteases would do.

Some experiments were done using highly purified enzymes (trypsinogen and amylase) and comparison with character of the protease extracts utilised by Yoneda et al. proves, that these phenomena are not identical and findings of the Japanese authors do not limit claims of the authors in any way. Utilisation of proenzymes instead of active proteases ensures for the organism in vivo conditions enabling protease effects normally observable in vitro (onkolyse, decrease of number of adhesive molecules, increase in tumour immumogenicity and suppression of metastase formation). The protease effect is of a fundamental character, effect of amylase is complementary. This approach is a way to ensure favourable conditions for final healing via the organismss's own immune system. This is why a modulatory intervention can be successful only if it was not preceded by major cytostatic and immunosuppressive therapy.

Examples of Practical Utilisation of the Invention

Methods

The following material and methods were used in the below mentioned examples, if not mentioned otherwise.

Mice

Female C57B16, mice (weight approx 24 g) were housed in plastic bins, fed the DOS 2b diet and given water ad libitum.

Protease Proenzymes and Amylase

Bovine pancreatic trypsinogen (EC 3.4.21.4) (SIGMA Co., USA) was highly purified (15000 BAEE (benzoyl-Arg-ethylester) units/mg of protein after activation to trypsin, which contained 430 BAEE units/mg of active trypsin protein).

Protein content: 97%

Partially purified porcine pancreatic trypsinogen was prepared by acid extraction and ammonium sulphate salting out according to Mansfeld et al. (Organopreprations 1958). Porcine pancreatic alpha-amylase (EC 3.2.1.1.), (SIGMA Co., USA) was a highly purified enzyme, double crystallised, 790 units/mg of protein ($E_{280}$ of 1% solution).

Pancreatic enzyme extract was prepared out of fresh porcine pancreatic glands by extraction with physiological saline and further purified on carboxymethylcellulose. Main products were trypsinogen and alpha-amylase, the ratio of which was adapted by addition of either purified trypsinogen or amylase for application to animals.

All preparations used for application to animals were dissolved or diluted by physiological saline.

Definition of Protease and Protease Proenzyme Activity and Methods of Determination.

Bovine Trypsinogen (SIGMA Co., USA) is declared by the manufacturer based on BAEE units (1 BAEE unit is defined as $A_{253}=0.001$ with BAEE as substrate at pH 7.6 and 25° C., reaction volume 3.2 ml, beam length 1 cm). Actual evaluation of trypsinogen (trypsin) activity was performed using synthetic chromogenic substrates, peptidic analogues of natural substrates (p-nitroanilides). The hydrolysed away p-nitroaniline represents measure of activity and its amount is determined spectrophotometrically at 405 nm/min and expressed in ankt/ml according to the formula:

$$ankt = \frac{A_{405} \times V \times \text{dilution} \times 100}{e \times v \times 60}$$

where V is volume of mixture at moment of determination, v=sample volume, e=extinction molar coefficient (10.4) for p-nitroaniline.

Temperature during determination=25° C. TRIS-Ca buffer (pH 7.6). The relationship between both methods of activity determination was established and expressed graphically. Concentration of protein was determined spectrophotometrically ($A_{280}$) and specific activity (grade of purity) was determined as relationship between activity and protein content. This value fully characterizes the preparation in regard to its relative enzyme purity.

Trypsin was determined using Z-Gly-Pro-Arg-p-nitroanilide. Chymotrypsin was determined using Glt-Ala-Ala-Pro-Phe-p-nitroanilide (-p-Na). Elastase was determined using Glt-Ala-Ala-Ala-p-Na and kallikrein using NO-Pro-Phe-Arg-p-Na. Aprotinin was determined through its trypsin inhibiting activity using Z-Gly-Pro-Arg-p-NA.

Because trypsinogen represents the basic component of each preparation (composition) and active trypsin activates all other pancreatic protease proenzymes present in the preparation, their determination is performed after trypsinogen activation using enteropeptidase (Borgstroem et al., Scand. J. Gastroenterol. 1993, Vol. 28, No. 5, p. 455).

Amylase Activity Definition and Determination Method

Commercial alpha-amylase (SIGMA, USA) is defined based on liberation of maltose from starch (1 unit liberates 1 mg of maltose from starch in 3 minutes at pH 6.9 and 20° C.). Amylase (alpha-amylase) was determined using a commercial kit (Slovakofarma Hlohovec, Slovakia) utilised for laboratory determination of alpha-amylase in blood serum and biological fluids. The tablet contains meshed starch with covalently bound dye, activator and buffer. Hydrolysis of insoluble bound starch leads to its solubilisation and it can be determined spectrophotometrically at 620 nm and expressed on ankt/ml or ankt/mg. Relationship between absorbance and activity is determined on a graph. The method is based on manufacturers instructions. Relationship between both methods of amylase activity determination was established and expressed graphically. Highly purified amylase was used as a standard.

Methylcholantrene Tumor Induction

The tumours were artificially induced in mice using methylcholantrene administered diluted in olive oil (100 ml of methylcholantrene is diluted under continuous stirring in 50 ml of olive oil). 0.2 ml of the oily substance (i.e. 400 ug of methylcholantrene) was applied subcutaneously per mouse. The application was repeated for three continuous days into the same location on the right flank, i.e. each mouse received 1.2 mg of methylcholantrene.

Tumor Induction through B16 Melanoma Cell Transplantation. Multiplication of Tumour Cells The transplanted tumour cells were grown as ascites in the peritoneal cavity. On day 10 after intraperitoneal transplantation of $2 \times 10^6$ cells the ascites was removed into Hanks solution, the cells were counted and diluted to a final concentration of $2 \times 10^6$ cells per 0.2 ml of suspension.

Transplantation and Progress of Tumour and Metastases

The suspension containing $2 \times 10^6$ cells per 0.2 ml of suspension was transplanted intradermally into the left flank of the mouse. On day 10 after melanoma B16 translantation the mice were narcotised by pentobarbital and tumours were removed. Day 10 for tumour excision was chosen based on preceding experimental determination of melanoma B16 activity, which found that if the primary tumour is removed on day 10 after transplantation of ascitic cells all mice will succumb in 5 weeks to effects of metastases.

EXAMPLE 1

Modulation of Primary Tumour and Survival Time:

A group of mice was used for this experiment, in which the tumour was induced by methylocholantrene (0.2 ml of oily suspension per mouse subcutaneously (400 μg of methylcholantrene). The application was repeated for three continuous days into the same location on the right flank, in other words each mouse received 1.2 mg of methylcholantrene. Tumours appeared on day 37–44 after application. On day 45 after the first application the group of mice was split into three experimental groups containing ten mice each and one control group of 8 mice. The control group was applied physiological saline instead of the compositions under study in the same intervals (24 hours) and volumes (0.1 ml).

The tested therapeutical substance was supplied in frozen form as substance A and B (specification see below). Both substances were thawed immediately before application and mixed 1:1. The tested substance was applied to the experimental mice subcutanously into a location as distant as possible from the induced tumour in a volume of 0.1 ml per mouse in intervals of 24 hours. The control group was applied physiological saline in volumes and intervals similar to the experimental groups.

Example 1 used 38 mice, which were randomised into 4 groups:

Exp.1.1 10 mice-application of solution A+B mix in standard dilution. Substance A as amylase in a concentration of 133.3 SIGMA units/ml. Substance B was trypsinogen in a concentration of 15000 BAEE units/ml (792 nkat/Z-Gly-Pro-Arg-p-nitroanilide).

Exp.1.2. 10 mice-application of A+B mix in a 10× higher concentration then the standard dilution.

Exp.1.3. 10 mice-application of A+B mix in a 30× higher concentration then the standard dilution.

Exp.1.4. 8 mice-control group, application of physiological saline in identical volumes and intervals.

Tumour size was measured twice weekly. Percentage of surviving mice was determined every day for 100 days. The results are shown in the following tables and graphs.

In the FIGURE, the filled squares represent data for Exp. 1.1; + marks represent data for Exp. 1.2; open squares represent data for Exp. 1.3; and * represents control data.

TABLE 1

Growth of Methylcholantrene Induced Tumours After Application of Therapeutic Substances A + B and in the Control Group.

Growth of Methylcholantrene Induced Tumours

| | Concentration of Substances A + B | | | | | | Control | |
|---|---|---|---|---|---|---|---|---|
| | Exp. 1.1 | | Exp. 1.2 | | Exp. 1.3 | | Exp. 1.4 | |
| Day | N | V | N | V | N | V | N | V |
| 1 | 9(10) | 6.3 | 10(10) | 10.8 | 7(10) | 14.0 | 8(8) | 10.5 |
| 5 | 10(10) | 44.2 | 10(10) | 39.1 | 10(10) | 39.1 | 8(8) | 34.5 |
| 8 | 10(10) | 39.1 | 10(10) | 33.9 | 10(10) | 34.4 | 8(8) | 62.9 |
| 12 | 10(10) | 50.7 | 10(10) | 47.6 | 9(10) | 40.3 | 8(8) | 67.4 |
| 15 | 10(10) | 56.0 | 10(10) | 43.8 | 8(10) | 51.3 | 8(8) | 80.3 |
| 17 | 10(10) | 31.9 | 10(10) | 23.9 | 8(10) | 38.8 | 8(8) | 87.1 |
| 19 | 10(10) | 35.5 | 10(10) | 40.6 | 8(10) | 74.0 | 8(8) | 80.8 |
| 22 | 10(10) | 48.0 | 10(10) | 66.2 | 8(10) | 66.9 | 8(8) | 98.6 |
| 26 | 10(10) | 36.7 | 10(10) | 57.9 | 8(10) | 94.6 | 8(8) | 88.5 |
| 29 | 10(10) | 62.1 | 10(10) | 50.3 | 8(10) | 97.6 | 8(8) | 106.0 |
| 33 | 10(10) | 74.3 | 10(10) | 63.5 | 8(10) | 83.6 | 8(8) | 114.6 |
| 36 | 10(10) | 113.0 | 10(10) | 105.1 | 8(10) | 150.1 | 8(8) | 184.0 |
| 40 | 10(10) | 130.0 | 10(10) | 148.6 | 8(10) | 155.9 | 7(7) | 174.0 |
| 43 | 10(10) | 120.8 | 10(10) | 108.2 | 7(9) | 102.4 | 7(7) | 253.1 |
| 47 | 10(10) | 160.7 | 10(10) | 168.8 | 6(9) | 126.5 | 7(7) | 253.1 |
| 50 | 10(10) | 204.8 | 10(10) | 196.3 | 6(9) | 163.2 | 6(6) | 365.0 |
| 54 | 8(9) | 205.1 | 10(10) | 277.6 | 6(9) | 183.7 | 4(5) | 388.3 |
| 57 | 8(9) | 254.8 | 9(9) | 276.7 | 6(9) | 213.5 | 3(4) | 251.3 |
| 61 | 7(8) | 289.9 | 8(8) | 328.0 | 6(9) | 273.5 | 2(3) | 328.0 |
| 64 | 7(8) | 301.9 | 6(7) | 424.3 | 7(9) | 391.7 | 2(3) | 332.0 |
| 68 | 6(6) | 429.8 | 4(4) | 471.0 | 6(8) | 443.2 | 0(0) | — |
| 71 | 4(4) | 234.0 | 3(3) | 337.7 | 6(8) | 428.3 | 0(0) | — |
| 75 | 4(4) | 262.5 | 3(3) | 384.7 | 4(6) | 489.8 | 0(0) | — |
| 78 | 4(4) | 400.5 | 3(3) | 461.3 | 2(4) | 656.5 | 0(0) | — |
| 82 | 3(3) | 565.0 | 3(3) | 494.3 | 3(4) | 836.0 | 0(0) | — |
| 85 | 3(3) | 871.7 | 2(2) | 963.0 | 2(3) | 565.0 | 0(0) | — |
| 89 | 3(3) | 1232 | 1(1) | 1575 | 2(3) | 600.5 | 0(0) | — |
| 92 | 2(3) | 1567 | 0(1) | — | 2(3) | 727.5 | 0(0) | — |
| 96 | 0(0) | — | 0(0) | — | 2(3) | 790.0 | 0(0) | — |
| 99 | 0(0) | — | 0(0) | — | 1(2) | 110.0 | 0(0) | — |
| Total Number of Animals Perished | 10 | | 10 | | 8 | | 8 | |
| Total Number of Animals Survived | 0 | | 0 | | 2 | | 0 | |

N comprises two values where x = number of measurable tumours, and y = number of mice in group. V = average tumour volume.

TABLE 2

Percetage of Animals Perishing from Methylcholantrene Induced Tumors

Percentage of Mice perished After Tumor induction

| | Concentration of Substances A + B | | | | | | Control | |
|---|---|---|---|---|---|---|---|---|
| | Exp. 1.1 | | Exp. 1.2 | | Exp. 1.3 | | Exp. 1.4 | |
| DAY | N | % | N | % | N | % | N | % |
| 40 | — | — | — | — | — | — | 1 | 12.5 |
| 43 | — | — | — | — | 1 | 10.0 | — | — |
| 54 | 1 | 10.0 | — | — | — | — | 2 | 37.5 |
| 57 | — | — | 1 | 10.0 | — | — | 1 | 50.0 |
| 61 | 1 | 20.0 | 1 | 20.0 | — | — | 1 | 62.5 |
| 64 | — | — | 1 | 30.0 | — | — | — | — |
| 65 | — | — | — | — | 1 | 20.0 | 1 | 75.0 |
| | 10(10) | | | | | | | |
| 66 | 1 | 30.0 | 3 | 60.0 | — | — | 1 | 87.5 |
| 67 | 1 | 40.0 | — | — | — | — | 1 | 100.0 |
| 71 | 2 | 60.0 | 1 | 70.0 | — | — | | |
| 75 | — | — | — | — | 2 | 40.0 | | |
| 78 | — | — | — | — | 2 | 60.0 | | |
| 82 | 1 | 70.0 | — | — | — | — | | |
| 85 | — | — | 1 | 80.0 | 1 | 70.0 | | |
| 88 | — | — | 1 | 90.0 | — | — | | |
| 94 | 1 | 80.0 | — | — | — | — | | |
| 95 | 1 | 90.0 | — | — | — | — | | |
| 96 | 1 | 100.0 | 1 | 100.0 | — | — | | |
| 97 | | | | | 1 | 80.0 | | |

TABLE 2-continued

Percetage of Animals Perishing from Methylcholantrene Induced Tumors
Percentage of Mice perished After Tumor induction

|  | Concentration of Substances A + B | | | | | | | Control |
|---|---|---|---|---|---|---|---|---|
|  | Exp. 1.1 | | Exp. 1.2 | | Exp. 1.3 | | Exp. 1.4 | |
| DAY | N | % | N | % | N | % | N | % |
| Total Number of Animals Perished | 10 | 100.0 | 10 | 100.0 | 8 | 80.0 | 8 | 100.0 |
| Total Number of Animals Survived | 0 | 0.0 | 0 | 0.0 | 2 | 20.0 | 0 | 0.0 |

Methylcholantrene was applied subcutaneously to 50 mice, a tumor appeared by 38, i.e. in 76%. Application was performed on mice, where tumours appeared between day 37–44 after application of first methylcholantrene dose. Mice with tumours were randomised into 3 experimental and one control Group. Average size of tumour in the beginning of the test was 10.4 mm$^2$.

Example 1.1.-Effect of Concentration "1" of A+B

The group consisted of 10 mice. In comparison, with control group growth of tumours was delayed (Table 1). While among the controls average tumour size exceeded "100" on day 29, among this experimental group this value was reached only on day 36, i.e. with 7 day delay. Average tumour size "200" was observed by the control group on day 43, in the experimental group on day 50, i.e. again a 7 day delay. An even more significant difference was observed in the survival of experimental and control mice (Table 2). On day 57 of the experiment when 50% of mice were dead 90% of the experimental mice were surviving. All mice of the control group perished by day 67 of the experiment (60% of experimental mice were still surviving by that day). Last mice with applied preparation perished on day 96, i.e. 29 days later.

Example 1.2.-Effect of Concentration "2" of A+B

The group consisted of 10 mice. In comparison with control group growth of tumours was delayed (Table 1). While among the controls average tumour size exceeded "100" on day 29, among this experimental group this value was reached only on day 36, i.e. with 7 day delay. Average tumour size "200" was observed by the control group on day 43, in the experimental group on day 50, i.e. again a 7 day delay. Concentration "2" of therapeutical substances A+B influenced the tumour with the same result as concentration "1".

An even more significant difference was observed in the survival of experimental and control mice (Table 2). On day 57 of the experiment when 50% of mice of the control group were dead 90% of the experimental mice were surviving. All mice of the control group perished by day 67 of the experiment (60% of experimental mice were still surviving by that day). Last mice with applied preparation perished on day 96., i.e. 29 days later.

Example 1.3.-Effect of Concentration "3" of A+B

The group consisted of 10 mice. In comparison with control group growth of tumours was delayed (Table 1). While among the controls average tumour size exceeded "100" on day 29, among this experimental group this value was reached only on day 36, i.e, with 7 day delay. Average tumour size "200" was observed by the control group on day 43, in the experimental group on day 57, i.e. a 14 day delay.

An even more significant difference was observed in the survival of experimental and control mice (Table 2). On day 57 of the experiment when 50% of mice of the control group were dead 90% of the experimental mice were surviving. All mice of the control group perished by day 67 of the experiment (80% of experimental mice were still surviving by that day). 2 mice survived day 100. i.e. 20% out of the total number.

Dilution "3" of therapeutic substances A+B was the most effective. Two mice were cured totally—by one of them a relapse appeared on day 100, when the experiment was terminated.

RESULT

It is evident from the data that application of tested substances A+B significantly influences survival of inbred C57B16 mice with a chemically induced tumour. While all control mice perished by day 67, out of experimental group 3 (highest concentration of administered substance) 20% of the mice survived longer than 100 days. Effect of the amount of effective substance is evident when comparing results of the individual groups. The best results were observed by mice with highest amount of administered substance (Exp. 1.3.).

EXAMPLE 2

Effect on Induction and Development of Metastases and Survival Times.

The substances were applied to inbred C57B16 mice with melanoma B16, which is syngeneic for the given line (i.e. no immunological barrier exists during transplantation) and has a high level of metastatic activity.

The transplanted tumour cells were grown as asictes in the peritoneal cavity. On day 10 after intraperitoneal transplantation of $2\times10^6$ cells the ascites were removed into Hanks solution, cells were counted and diluted to a final concentration of $2\times10^6$ cells per 0.2 ml of suspension.

The suspension containing $2\times10^6$ cells per 0.2 ml of suspension was transplanted intradermally into the left flank of the mouse. On day 10 after melanoma B16 transplantation the mice were narcotised by pentobarbital and tumours were removed. Day 10 for tumour excision was chosen based on preceding experimental determination of melanoma B16 activity, which found that if the primary tumour is removed on day 10 after transplantation of ascitic cells all mice will succumb in 5 weeks to effects of metastases.

Tested substances were stored frozen at $-20°$ C. They were thawed immediately before application and brought to body temperature. Substances "A" and "B" (specification same as in Exp.1.1.) were mixed 1:1, substance "C" (see below) was applied as such. The tested substance was administered to the experimental ice subcutaneously into a location as distant as possible from the induced tumour in a volume of 0.1 ml or 0.05 ml per mouse in intervals of 24 or 48 hours. The control group was applied physiological saline in volumes and intervals similar to the experimental groups.

Survival of mice was monitored every day for 100 days. Dead mice were marked, stored in formaldehyde solution until section was performed (for determination of exitus cause and number of metastases).

Description of substances "A" and "B" is similar to Example 1. Substance "C" is a partially purified pancreatic extract. Its amylolytic activity and trypsinogen content are similar to the A+B mix. Besides that it contains a certain amount of chymotrypsinogen.

Example 2.1.

Experimental group consisted of 10 mice. 0.1 ml of therapeutic substance A+B was applied subcutaneously in intervals of 24 hours. On day 22 of the experiment 22 mice perished (20% of the total), on day 25, one mouse perished (10% of the total), on day 28 one mouse perished (10% of the total), on day 36 one mouse perished (10% of the total) and one day 42 one mouse perished (10% of the total). 100 days were survived by 4 mice, i.e. 40% out of the total number of 10 animals.

Example 2.2.

Experimental group consisted of 10 mice. 0.1 ml of therapeutic substance A+B was administered subcutaneously in intervals of 48 hours. On day 22 of the experiment, one mouse perished (10% of the total), on day 34 one mouse perished (10% of the total), on day 38 one mouse perished (10% of the total) and on day 40 one mouse perished (10% of the total). 100 days were survived by 6 mice, i.e. 60% of the total number of 10 animals.

Example 2.3.

Experimental group consisted on 10 mice. 0.05 ml of therapeutic substance A+B was administered subcutaneously in intervals of 48 hours. On day 12 of the experiment, one mouse perished (10% of the total), on day 16 one mouse perished (10% of the total), on day 23 two mice perished (20% of the total), on day 28 one mouse perished (10% of the total), on day 33 one mouse perished (10% of the total), on day 35 one mouse perished (10% of the total) and finally on day 39 one mouse perished (10% of the total). 100 days were survived by 2 mice, i.e. 20% out of the total number of 10 animals.

Example 2.4

Control group consisted on 6 mice. 0.1 ml of physiological saline was administered subcutaneously in intervals of 48 hours. On day 12 of the experiment, one mouse perished (10% of the total), on day 17 one mouse perished (16.6% of the total), on day 18 two mice perished (3.2% of the total), on day 23, 29 and 34 each one mouse perished (i.e. in each case 16.6% of the total). 100 days were survived by no mice, i.e. whole 100% of the control group perished.

Example 2.5-First Control Group

Experimental group consisted of 10 mice. 0.05 ml of substance A alone was administered subcutaneously in intervals of 48 hours. On day 24 of the experiment 1 mouse perished (10% of the total), on day 26 one mouse perished (10% of the total), on day 27 one mouse perished (10% of the total), on day 33 one mouse perished (10% of the total), on day 35 one mouse perished (10% of the total), on day 37 one mouse perished (10% of the total), on day 39 one mouse perished (10% of the total) and on day 47 one mou se perished (10% of the total). 100 days were survived by 2 mice, i.e. 20% out of the total number of 10 animals.

Example 2.6-Second Control Group

Experimental group consisted of 10 mice. 0.05 ml of substance B alone was administered subcutaneously in intervals of 48 hours. On day 23 of the experiment 2 mice perished (20% of the total), on day 25 one mouse perished (10% of the total), on day 26 one mouse perished (10% of the total), on day 30 one mouse perished (10% of the total), on day 31 one mouse perished (10% of the total), on day 34 one mouse perished (10% of the total) and on day 50 one mouse perished (10% of the total). 100 days were survived by 2 mice, i.e. 20% out of the total number of 10 animals.

Example 2.7.

Experimental group consisted of 10 mice. 0.1 ml of substance C was administered subcutaneously in intervals of 48 hours. On day 36 of the experiment 1 mouse perished (10% of the total), on day 38 one mouse perished (10% of the total) and on day 43 one mouse perished (10% of the total). 100 days were survived by 6 mice, i.e. 60% out of the total number of 10 animals.

Example 2.8.-Third Control Group

Control group consisted of 14 mice. 0.1 ml of physiological saline was administered subcutaneously in intervals of 48 hours. On day 5 of the experiment 1 mouse perished (7.1% of the total), on day 15 two mice perished (14.3% of the total), on day 19 one mouse perished (7.1 of the total), on days 20, 21, 23, 27 and 29 each one mouse perished (i.e. in each case 7.1% of the total), on day 30 two mice perished (14.3% of total) and on day 31 and 32 each one mouse perished (i.e. in each case 7.1% of the total). 100 days were survived by no mice, i.e. all 100% of the 14 members of the control group perished.

Example 2.8.-Control Group

Control group consisted of 14 mice. This group served to monitor survival after excision of melanoma B16 excision. The tumour was excised on day 10 after intradermal transplantation of $2 \times 10^6$ ascitic cells.

Mice survival (see Table 4)

No mice survived 100 days, i.e. 0%.

The results are summarised in the following tables 3 and 4.

TABLE 3

Results of Examples 2.1.–2.8

| Example | Number of Mice | Substance Type | Dose (ml) | Interval H | Exitus Total | Day | Survived 100 days | % |
|---------|----------------|----------------|-----------|------------|--------------|-----|-------------------|---|
| 2.1 | 10 | A + B | 0.1 | 24 | 6 | 22-2<br>25-1<br>28-1<br>36-1<br>42-1 | 4 | 40 |
| 2.2 | 10 | A + B | 0.1 | 48 | 4 | 22-1<br>34-1<br>38-1<br>40-1 | 6 | 60 |
| 2.3 | 10 | A + B | 0.05 | 48 | 8 | 12-1<br>16-1<br>23-2<br>28-1<br>33-1<br>35-1<br>39-1 | 2 | 20 |
| 2.4 | 6 | Phys sol | 0.1 | 48 | 6 | 17-1<br>19-2<br>23-1<br>29-1<br>35-1 | 0 | 0 |
| 2.5 | 10 | A | 0.05 | 48 | 8 | 24-1<br>26-1<br>27-1<br>33-1<br>35-1<br>37-1<br>39-1<br>47-1 | 2 | 20 |
| 2.6 | 10 | B | 0.05 | 48 | 8 | 23-2<br>25-1<br>26-1<br>30-1<br>31-1<br>34-1<br>50-1 | 2 | 20 |
| 2.7 | 10 | C | 0.1 | 48 | 4 | 36-1<br>38-1<br>42-1<br>43-1 | 6 | 60 |

TABLE 3-continued

Results of Examples 2.1.–2.8

| Example | Number of Mice | Substance Type | Dose (ml) | Interval H | Exitus Total | Day | Survived 100 days | % |
|---|---|---|---|---|---|---|---|---|
| 2.8 | 14 | Phys sol. | 0.1 | 48 | 15 | 5-1<br>15-2<br>19-1<br>20-1<br>22-1<br>23-1<br>27-1<br>29-1<br>30-2<br>31-1<br>32-1 | 0 | 0 |

TABLE 4

Mice Succumbing to Metastases after Excision of the Primary Tumor

| Day | Number of Ex | Percentage Perished | Percentage Surviving |
|---|---|---|---|
| 5 | 1 | 7.14 | 92.86 |
| 15 | 2 | 21.43 | 78.57 |
| 19 | 1 | 28.57 | 71.43 |
| 20 | 1 | 35.71 | 64.29 |
| 21 | 1 | 42.86 | 57.14 |
| 22 | 1 | 50.00 | 50.00 |
| 23 | 1 | 57.14 | 42.86 |
| 27 | 1 | 64.29 | 35.71 |
| 29 | 1 | 71.43 | 28.57 |
| 30 | 2 | 85.71 | 14.29 |
| 31 | 1 | 92.86 | 7.14 |
| 32 | 1 | 100.000 | 0.000 |
| Out of 14 mice ex | 14 | 100.00 | 0.00 |

CONCLUSION

It is evident from the results that substances "A+B" and substance "C" inhibit induction of melanoma B16 metastases. For the combination "A+B" the dosage 0.2 ml/20 mg and time interval of 48 hours was found to be best, 60% of the test animals survived with this regimen longer than 100 days, while control group 2.5 died out by day 35 of the experiment and the second extended control group 2.9 perished by day 32.

Because melanoma B16 represents an aggressive metastasing tumour on inbred C57B16 mice are the results obtained using amylase+trypsinogen and pancreatic extract positive and the substances have a promising antitumour effect.

We claim:

1. A pharmaceutical preparation with an inhibitory effect on malignant tumors, comprising:

a malignant tumor inhibitory effective amount of a mixture of an isolated and inactive protease proenzyme selected from the group consisting of trypsinogen, chymotrypsinogen, proelastase, and prekallikrein;

amylase; and aprotinin;

wherein said protease proenzyme and said amylase are present in a ratio from 1:100 to 100:1 in units of enzymatic activity.

2. The pharmaceutical preparation of claim 1, wherein said amylase is of human, animal, bacterial or plant origin.

3. The pharmaceutical preparation of claim 1, wherein said protease proenzyme is of human or animal origin.

* * * * *